United States Patent [19]

Griffith

[11] 4,378,248

[45] Mar. 29, 1983

[54] BONDING DENTAL PORCELAIN

[76] Inventor: Jack R. Griffith, 10 Golders St., Heidelberg, Victoria, 3084, Australia

[21] Appl. No.: 279,206

[22] Filed: Jun. 30, 1981

[30] Foreign Application Priority Data

Jul. 2, 1980 [AU] Australia .............................. PE4335

[51] Int. Cl.$^3$ ................................................ C09K 3/00
[52] U.S. Cl. .................................. 106/35; 260/998.11; 264/16; 433/199; 433/202; 433/228; 501/57
[58] Field of Search ...................... 106/35; 501/57, 73; 260/998.11; 433/228, 199, 202; 264/16

[56] References Cited

U.S. PATENT DOCUMENTS 4,123,416 10/1978 Potter et al. .......................... 106/35

OTHER PUBLICATIONS

Modern Practice in Dental Ceramics, Johnston et al., pp. 4–13 (1967).
The Science and Art of Dental Ceramics, J. W. McLean, pp. 23–41 (1979).

*Primary Examiner*—Lorenzo B. Hayes
*Attorney, Agent, or Firm*—Hill, Van Santen, Steadman, Chiara & Simpson

[57] ABSTRACT

The bonding of smooth dental porcelain using glass-ionomer cement has hitherto been difficult. The present invention incorporates particles of an ion-leachable glass, particularly a calcium fluoroaluminosilicate glass, in the dental porcelain and improves the bonding properties.

6 Claims, No Drawings

BONDING DENTAL PORCELAIN

FIELD OF THE INVENTION

The present invention relates to a method of bonding dental porcelain using a glass-ionomer or polycarboxylate cement, a dental porcelain having improved bonding properties, and a composition for making up the porcelain.

BACKGROUND OF THE INVENTION

It is now recognised that so-called glass-ionomer and polycarboxylate cements may be potentially the most efficient and suitable substances yet developed for dental cementation.

Glass-ionomer cements generally comprise a mixture of an ion-leachable glass in particulate form together with a cross-linkable poly(carboxylic acid). When a solvent is added to the cement, multivalent ions become leached from the glass and cross-link the poly(carboxylic acid) during curing. It has been shown that such glass ionomer cements exhibit a degree of adhesion to enamel, dentine and specially surface treated platinum and gold alloys. However, it has been reported that the glass-ionomer cements do not bond to any significant degree to porcelain and are thus precluded from use in dental restorative systems utilising ceramic materials. This work is discussed in Hotz et al., British Dental Journal 142:2 41–47 (January) 1977. Such glass ionomer cements are commercially available under the trade marks ASPA and FUJI ionomer.

Polycarboxylate cements similarly involve the cross-linking of a poly(carboxylic acid) by means of multivalent ions. However, in this case the poly(carboxylic acid) is mixed with zinc oxide particles, which normally include a minor proportion of magnesium oxide. Commercially available polycarboxylate cements include Durelon (available from ESPE) and PCA (available from S. S. White).

SUMMARY OF THE INVENTION

It is an object of the present invention to produce a porcelain capable of being bonded by means of glass-ionomer or polycarboxylate cements.

Thus, the present invention provides a dental porcelain having incorporated therein a particulate ion-leachable glass.

The invention also provides in a further aspect a composition for making up such a dental porcelain which comprises dental porcelain powder in intimate admixture with particles of an ion-leachable glass.

In a still further aspect, the present invention provides a method of bonding dental porcelain using a glass ionomer or polycarboxylate cement, which comprises incorporating in the dental porcelain particles of an ion-leachable glass, and bonding the porcelain by application thereto of the cement.

Calcium fluoroaluminosilicate glasses are well known ion-leachable glasses and may be prepared by fusing a mixture of calcium oxide, aluminium oxide, silica and a fluoride to form a glass. Such glass when reduced to particulate form and mixed with a poly(carboxylic acid) forms a water-hardenable cement. Thus, when water is added to the cement, calcium ions leach from the glass and crosslink the poly(carboxylic acid) chains. A particle size of 100 to 400 microns (e.g. 150 to 200 microns) is generally preferred.

However, whilst calcium fluoroaluminosilicate glasses have been mentioned specifically, it will be understood that any ion-leachable glass capable of crosslinking a poly(carboxylic acid) is envisaged. A variety of such glasses is known in the art.

The poly(carboxylic acid) is generally a long chain polymer having a plurality of carboxylic acid molecules. Usually, it is prepared by polymerising a vinyl unsaturated carboxylic acid, such as acrylic acid or methacrylic acid. Generally, the poly(carboxylic acid) is a poly(acrylic acid).

The dental porcelain may be made up by mixing particles of calcium fluoroaluminosilicate glass with dental porcelain powder to form a composition, and then firing the composition to form the dental porcelain. Preferably, the unfired porcelain in the form of a slurry is vibrated into moulds so that the glass particles sink to the bottom of the slurry and may be more readily exposed after firing. Usually, the porcelain composition is fired at 610° to 930° C. in a vacuum furnace. Preferably, the glass particles constitute from 10 to 65% by weight of the dental porcelain, preferably from 20 to 35% by weight.

After firing the surface of dental porcelain is preferably lightly abraded so as to expose the incorporated glass particles and facilitate contact with the cement.

Prior to firing, the dental porcelain is usually formed into an appropriate shape, e.g. a facing, for use in a dental restorative operation. The slurry including the glass particles may be applied as the first layer when a porcelain inlay, porcelain jacket crown or facing is being built up. Normal additional layers of conventional porcelain may then be built up on the first layer. The glass particles are thus usually only incorporated in the outer layer of porcelain which is to contact the cement.

The side of the porcelain which has been roughened to expose the glass particles is then coated with the cement and adhered in place. It will be appreciated that the dental porcelain may be provided in any desired shape appropriate to any particular restorative operation and that generally only those surfaces which are to be adhered will be subjected to abrading.

The formulation of suitable dental porcelain powders is well known to the man in the art and forms no part of the present invention. In this specification, the term "dental porcelain" is used to refer to the porcelain produced after firing.

DESCRIPTION OF PREFERRED EMBODIMENTS

Embodiments of the present invention will now be described by way of example only and in comparison with prior art bonding techniques.

General Method

Vita VMK 68, 542 dentine porcelain powder was chosen as a representative ceramic material. The ASPA glass particles and ASPA cementing material were as supplied under the trade name ASPA Special Luting Material (obtainable from Smith & Nephew Ltd.)

The ASPA powder cementing material was prepared by mixing with water for 30 seconds using a powder to liquid ratio of 2 grams to 1.32 grams.

The dentine porcelain powder was first made up into a slurry, with or without addition of glass particles. The unfired porcelain slurry was placed into polyether moulds so as to form small discs 10 mm in diameter, and the slurry vibrated. The porcelain was fired at 610° C.

to 930° C. in a Panamat vacuum furnace. After firing, each porcelain disc was cemented between a pair of metal rods for linking to a load testing machine. One side of each disc was attached to a first metal rod by means of a rapid curing epoxy resin. The second metal rod was provided with a double undercut cavity. The double undercut cavity was filled with the mixed ASPA cementing material and the other side of the disc attached. The assembly was then placed in a holding jig and allowed to set under ambient conditions. After 10 minutes, the cemented assemblies were coated with cavity varnish and transferred to an atmosphere of 37° C. and a 100% relative humidity for 24 hours in order to condition. The two metal rods were then placed in the jaws of a Shimadzu 10T load cell universal testing machine and the breaking stresses established. The results are given in Tables 1 and 2.

Comparison Tests A and B (a) Smooth Porcelain

The surface of the fired disc was lightly abraded with a finishing disc prior to cementing of the disc to the second metal rod with the ASPA cementing material.

(b) Rough Porcelain

In order to produce a suitable surface with a consistent roughness, the porcelain slurry was vibrated in the mould against discs of electroformed gold deposited under predetermined conditions, so as to produce the required consistent irregular surface. In order to improve wetting of the gold surface by the porcelain slurry, the electroformed gold was lightly tin plated prior to application of the porcelain slurry. The porcelain and gold discs were then fired. After firing, the gold was etched away from the porcelain disc with aqua regia so as to leave an irregular surface on the porcelain. The irregular porcelain surface was abraded and then cemented to the second metal rod using the ASPA cementing material.

EXAMPLES 1 TO 3

In these examples 20, 33 and 50% by weight of ASPA glass particles of particle size 150 to 200 microns were added to the porcelain slurry prior to firing.

The smooth and rough porcelain surfaces were prepared as described in the Comparison Test. The surfaces of the fired discs were lightly abraded to expose the included glass particles, before the discs were cemented to the second rod using the ASPA cementing material.

The results of the strength test measurements are given in Table 1.

EXAMPLES 4 TO 6

In these Examples 25, 33 and 50% by weight of ion-leachable glass particles of particle size 150 to 200 microns were added to the porcelain slurry prior to firing. The glass was formed by melting together the following components:

| Component | Percentage (by weight) |
|---|---|
| $Al_2O_3$ | 16–20 |
| $SiO_2$ | 28–34 |
| $AlPO_4$ | 8–12 |
| $Na_3AlF_6$ | 20–25 |
| $AlF_3$ | 3–6 |

| Component | Percentage (by weight) |
|---|---|
| $CaF_2$ | 10–20 |

Porcelain discs incorporated in the glass particles were prepared as before and cemented to the metal rods using the ASPA cement. The strength test measurements are given in Table 2.

TABLE 1

| Example | Percentage Glass Addition | Breaking Stress MPa (mega Pascals) | |
|---|---|---|---|
| | | Smooth Porcelain | Rough Porcelain |
| Comparison A | 0 | 0 | 1.75 |
| 1 | 20 | 1.67 | 1.80 |
| 2 | 33 | 1.72 | 1.64 |
| 3 | 50 | 2.03 | 1.84 |

TABLE 2

| Example | Percentage Addition | MPa | |
|---|---|---|---|
| | | Smooth Porcelain | Rough Porcelain |
| Comparison B | 0 | 0 | 1.20 |
| 4 | 25 | 1.48 | 1.64 |
| 5 | 33 | 1.55 | 1.58 |
| 6 | 50 | 1.88 | 1.70 |

The results may be summarised as follows: No attachment whatever was obtained between the ASPA cementing material (comprising a mixture of glass particles, water and poly(carboxylic acid)) and smooth porcelain. The porcelain with the specially prepared irregular surface but without addition of glass particles showed good strength. However, it is not normally practical to prepare such an irregular surface. The results for the smooth porcelain to which glass particles had been added shows that the incorporation of the glass particles in the porcelain produces a degree of attachment, with the result generally increasing with increasing percentage addition of glass particles. The results obtained with the rough porcelain to which glass particles had been added were similar to those obtained with no glass addition and did not appear to be influenced by the percentage of glass added.

The results show that by the incorporation of ion-leachable glass particles into the porcelain, a good bond may be obtained between the porcelain and a glass-ionomer cement even when the porcelain has a smooth surface. If the glass particles are not incorporated, it is not possible to obtain any bonding between the smooth porcelain and the cement.

We claim:

1. A composition useful for the preparation of a dental porcelain, said porcelain being capable of being bonded by means of a cement comprising a poly(carboxylic acid) which composition comprises a dental porcelain powder suitable for the production of dental porcelain;

an ion-leachable glass in particulate form in intimate admixture with said dental porcelain powder;

said ion-leachable glass in admixture with said porcelain powder being a calcium fluoroaluminosilicate glass having a particle size in the range 100–400 microns, and said ion-leachable glass particles constituting 10 to 65% by weight of said composition.

2. A fired and shaped dental porcelain containing dental porcelain powder and having incorporated therein an ion-leachable glass in particulate form, the porcelain being capable of being bonded by means of a cement comprising
   a poly(carboxylic acid), wherein
   said ion-leachable glass is a calcium Fluoroaluminosilicate glass having a particle size in the range 100–400 microns, and
   said ion-leachable glass particles constitute 10 to 65% by weight of said porcelain.

3. A dental porcelain according to claim 2 wherein the glass particles are concentrated at a region of said porcelain adjacent a surface thereof to be bonded by said cement.

4. A dental porcelain according to either of claims 2 or 3 wherein a surface of said porcelain to be bonded by said cement has been abraded to expose particles of said ion-leachable glass.

5. A method for the preparation of a dental porcelain, said porcelain being capable of being bonded by means of a cement comprising a poly(carboxylic acid), which method comprises:
   (1) admixing a slurry comprising a dental porcelain powder with a particulate ion-leachable glass, said ion-leachable glass in admixture with said porcelain powder being a calcium fluoroaluminosilicate glass having a particle size in the range 100–400 microns, and said glass particles constituting 10 to 65% by weight of said admixture;
   (2) shaping the admixture into the desired form and
   (3) firing said formed admixture.

6. A method according to claim 5 which comprises the step of vibrating said admixture in a mould prior to firing, whereby particles of said glass settle and are concentrated in a region of said porcelain adjacent a surface thereof which is to be bonded by said cement.

* * * * *